(12) United States Patent
Herting et al.

(10) Patent No.: US 8,048,043 B2
(45) Date of Patent: Nov. 1, 2011

(54) METHOD OF ADMINISTRATION OF A PULMONARY SURFACTANT

(75) Inventors: Egbert Herting, Parma (IT); Wolfgang Gopel, Parma (IT); Paolo Chiesi, Parma (IT)

(73) Assignee: Chiesi Farmaceutici S. P. A., Parma (IT)

( * ) Notice: Subject to any disclaimer, the term of this patent is extended or adjusted under 35 U.S.C. 154(b) by 966 days.

(21) Appl. No.: 11/811,351

(22) Filed: Jun. 8, 2007

(65) Prior Publication Data

US 2008/0305180 A1    Dec. 11, 2008

(51) Int. Cl.
*A61M 25/00*    (2006.01)

(52) U.S. Cl. ............... 604/264; 604/93.01; 128/204.18; 128/207.18; 424/557

(58) Field of Classification Search ................. 424/557; 128/204.18, 207.18; 604/93.01, 264
See application file for complete search history.

(56) References Cited

U.S. PATENT DOCUMENTS

| 5,552,161 A * | 9/1996 | Disse et al. ................. 424/557 |
| 2004/0020488 A1 * | 2/2004 | Kniewasser ............ 128/204.18 |
| 2006/0040860 A1 * | 2/2006 | Ruediger et al. .............. 514/12 |

FOREIGN PATENT DOCUMENTS

GB    2307412 A  *  5/1997

OTHER PUBLICATIONS

Apexmed Catalog. "Endotracheal tube <Murphy> type." 2004. 2 pages.*

* cited by examiner

*Primary Examiner* — Allison M Ford
*Assistant Examiner* — Susan E Fernandez
(74) *Attorney, Agent, or Firm* — Ladas & Parry LLP

(57) ABSTRACT

The present invention concerns a method for treating a respiratory distress in a infant in need of such treatment, the method comprising intratracheal administration of a pulmonary surfactant by a thin tube.

The invention also concerns a kit for performing said method.

13 Claims, No Drawings

METHOD OF ADMINISTRATION OF A PULMONARY SURFACTANT

FIELD OF INVENTION

The present invention concerns a method for preventing and/or treating respiratory distress syndrome in infants in need of such treatment, the method comprising intratracheal administration of a pulmonary surfactant by a thin tube.

The invention also concerns a kit for performing said method.

BACKGROUND OF THE INVENTION

The human lung is composed of a large number of small air sacs, called alveoli, in which gases are exchanged between the blood and the air spaces of the lungs. In healthy individuals, this exchange is mediated by the presence of a protein-containing surfactant complex that prevents the lungs from collapsing at the end of expiration.

Lung surfactant complex is composed primarily of lipids and contains minor amounts of various proteins. An absence of adequate levels of this complex results in malfunction of the lung. This syndrome is called Respiratory Distress Syndrome (RDS) and is the single most important cause of morbidity and mortality in pre-term infants.

RDS is mainly treated with replacement therapy whereby exogenous pulmonary surfactant preparations extracted from animal lungs, known as modified natural surfactants are administered to the human in need. For instance, modified natural surfactants used in the clinical practice are poractant alfa derived from porcine lung, and sold under the trademark of Curosurf®, beractant (Surfacten® or Survanta®) bovactant (Alveofact®), both derived from bovine lung, and calfactant derived form calf lung (Infasurf®).

Synthetic surfactants mimicking the composition of the modified natural surfactants, and known as reconstituted surfactants, have also been developed.

Exogenous pulmonary surfactants are currently administered by endotracheal instillation as suspension in a saline aqueous solution to intubated pre-term infants kept under intermittent positive pressure ventilation (IPPV).

However, IPPV is in itself an invasive procedure which frequently requires supplemental medication like treatment with sedatives, analgesic agents and catecholamines.

Furthermore IPPV in pre-term infants with RDS has long been recognized to contribute to lung injury which may lead to the development of pneumothorax and/or bronchopulmonary dysplasia (BDP); and may cause reduction of mucociliary clearance, mucosal injury, and secondary infections as well as blockage of the endotracheal.

In view of the potential complications associated with intubation and mechanical ventilation, attention has been focused on different approaches of administration of exogenous surfactant.

Since long time, as a possible initial respiratory support for very low birth weight (VLBW) infants, use of early nasal Continuous Positive Airway Pressure (nCPAP), that delivers air into the lungs through specially designed nasal devices such as masks, prongs or tubes, has been introduced in neonatal intensive care.

Recently, to give exogenous surfactant without mechanical ventilation, the use of a thin gastric tube placed in the trachea supported with nCPAP has been proposed (Göpel W et al, abstract presented at the 20th International Workshop on Surfactant Replacement, Belfast, Jun. 2-5, 2005, page 12: Kribs, A et al. Paediatr Anaesth. April 2007; 17(4):364-9.).

In particular, Göpel W and colleagues reported on the administration of 60 mg bovine surfactant, diluted to 30 mg/ml, by a 5 Fr gastric tube in spontaneously breathing infants with a mean weight of about 1 kg.

However, to improve the clinical outcome, an initial dose higher than 60 mg/kg body weight, is currently recommended. A dose higher than 60 mg/kg requires a higher concentration of the surfactant preparation to be used, in particular of at least 40 mg/ml.

Since viscosity increases with surfactant concentration, the administration of a concentration of at least 40 mg/ml, by means of a gastric tube that has a very small diameter (5 Fr. corresponds to about 1.7 mm) would be only possible with a surfactant having low viscosity. In fact high viscosities would make the passage of the surfactant through the gastric tube and the small airways more difficult and may therefore result in uneven distribution in the lungs of the pre-term infants. Theoretically, surfactants having high viscosities carry the risk of blockage of the gastric tube and of acute airway obstruction.

In view of the drawbacks of the methods previously used for delivery of exogenous surfactant, alternative therapeutic methods for surfactant administration are needed. Such methods should provide at least identical or, preferably improved clinical outcome without the potential complications associated to endotracheal intubation and mechanical ventilation.

The therapeutic methods and kits disclosed herein provide a real improvement over therapies described in the art.

SUMMARY OF THE INVENTION

The present invention contemplates a method for preventing and/or treating a respiratory distress syndrome in a patient in need of such treatment, said method comprising the steps of:

a) applying nasal Continuous Positive Airway Pressure (nCPAP) with a nasal device to said infant at a pressure of from 1 to 12 cm water;

b) administering a pulmonary surfactant suspended in a pharmaceutically acceptable aqueous medium via a tube having a diameter comprised between 5 and 12 Fr, preferably a gastric tube, into the trachea of said infant; and c) removing said tube at the end of the administration;

wherein the surfactant suspension is applied at a concentration of at least 40 mg/ml and has a viscosity lower than 20 mPas.

The invention is also directed to a kit comprising: a) a sterile pharmaceutical composition comprising a pulmonary surfactant having a viscosity lower than 20 cpoise suspended in a pharmaceutically acceptable aqueous medium at a concentration of at least 40 mg/ml; b) a thin tube having a diameter comprised between 5 and 12 Fr; c) a device for administering the surfactant at a controlled rate; and d) container means for containing the dosage form, the thin tube and the device.

DEFINITIONS

The term "modified natural surfactant" means a lipid extract of minced mammalian lung which, due to the lipid extraction step used in the manufacture process, is deprived of the hydrophilic proteins SP-A and SP-D and contains variable amounts of the hydrophobic proteins SP-B and SP-C. Depending on the method of extraction, the preparation may contain non-surfactant lipids and other components.

The term "reconstituted surfactant" means a synthetic surfactant made of a mixture of polar lipids, primarily phospholipids and optionally other components such as neutral lipids to which have been added surfactant proteins/peptides isolated from animals or proteins/peptides manufactured through recombinant technology such as those described in WO 95/32992, or synthetic surfactant protein analogues such as those described in WO 89/06657, WO 92/22315 and WO 00/47623.

"Pharmaceutical acceptable" is a term used herein that refers to a medium that does not produce an allergic or similar untoward reaction when administered to an infant.

The expression "improving the clinical outcome" means a surfactant with an improved efficacy in terms of indices of activity, i.e lung compliance, lung gas volume, blood gases and ventilator settings.

DETAILED DISCLOSURE OF THE INVENTION

The present invention discloses a method of preventing and/or treating a respiratory distress syndrome, said method comprises the steps of:

a) applying nasal Continuous Positive Airway Pressure (nCPAP) with a nasal device to said infant at a pressure of about 1 to 12 cm water;

b) administering a pulmonary surfactant suspended in a pharmaceutically acceptable aqueous medium via a tube having a diameter comprised between 5 and 12 Fr into the trachea of said infant; and c) removing said tube at the end of the administration;

wherein the surfactant suspension is applied at a concentration of at least 40 mg/ml and has a viscosity lower than 20 mPas.

Advantageously, the method of the invention is applied to pre-term very-low-birth-weight-infants infants of 24-35 weeks gestational age that are spontaneously breathing, and demonstrate early signs of respiratory distress syndrome as indicated either by clinical signs and/or supplemental oxygen demand (fraction of inspired oxygen ($FiO_2$)>30%). The treatment shall start preferably in the first 24 h of life.

The method of the invention is directed to the prevention and/or treatment of the respiratory distress syndrome on the infant related to a surfactant-deficiency or dysfunction (RDS) as well as of conditions in which respiratory distress may be present that include, but are not limited to, meconium aspiration and pulmonary infection.

The method of the invention may also be useful for preventing and/or treating acute respiratory distress syndrome in children or adults.

The method of the invention comprises applying nasal Continuous Positive Airway Pressure (nCPAP) with a nasal device such as a mask, prongs, or a pharyngeal tube according to procedures well known to the person skilled in the art.

Preferably a nasal mask is utilised. Any nasal mask commercially available may be used, for example those provided by The CPAP Store LLC, and the CPAP Company.

Nasal CPAP is typically applied at a pressure comprised between 1 and 12 cm water, preferably 2 and 8 cm water, although the pressure can vary depending on the infant and the pulmonary condition.

The application of nCPAP is advantageously carried out to the infant prior to administering the surfactant and continuously throughout the procedure during both the administering and the removing steps.

Optionally, prior to the procedure, atropine is administered i.v. at 5 μg/kg body weight. Sedative and/or analgesic drugs can optionally be administered as well.

Before administering the pulmonary surfactant, the gastric tube is placed with a Magill-forceps under direct visualization of the vocal cords of the infants by means of a laryngoscope.

After placement of the gastric tube, the laryngoscope is removed and the pulmonary surfactant is administered by instillation in the trachea at controlled rate with a suitable device.

The pulmonary surfactant in the form of suspension is administered by means of a tube having a diameter comprised between 5 and 12 Fr.

Any gastric or nasogastric tube, arterial or suction catheter of common use in the hospital can be utilised for the purpose of the invention.

The tube may be made of any material, preferably of polyurethane or silicone.

Preferably a 5 Fr tube is used because it has a small diameter, but at the same time it is stiff enough to allow easy introduction with the Magill forceps. Preferably a cm-scale is marked on the tube to allow the correct length of introduction.

If the tube has side holes, such holes should not be too far away from the catheter tip. The connector to the syringe should be small too avoid unnecessary dead space.

Preferably the tube has a total length of about 30 cm to allow a length of about 10 cm in the oral cavity/nasopharynx and a length of about 20 cm outside for easy handling.

Suitable devices include syringes having a small dead volume, preferably of less than 0.5 ml, more preferably of less than 0.3 ml or, infusion pumps.

Depending of the volume to be administered, the person skilled in the art shall control the rate of delivering of the device so as to instil the surfactant in a time ranging from 1 to 5 minutes, preferably from 1 to 3 minutes.

The pulmonary surfactant is administered as a suspension in a sterile pharmaceutically acceptable aqueous medium, preferably in a buffered physiological saline aqueous solution, more preferably buffered at a pH from 5.5 to 6.5.

The concentration of the surfactant is of at least 40 mg/ml, preferably from 40 to 80 mg/ml.

The applied volume should be not more than 3.0 ml, preferably not more than 2 ml and depending on the concentration of the surfactant and dead volume of the syringe.

Any modified natural- or reconstituted surfactant can be used provided that the relevant suspension in an aqueous medium has a viscosity lower than 20 mPas (1 mPas corresponds to 1 centipoise), preferably comprised between 5 and 15 mPas, more preferably comprised between 6 and 10 mPas.

The viscosity may be determined by any known method. Preferably, the viscosity is determined according to the method reported in Example 1.

In particular, it has been found that, due to its low viscosity, the modified natural surfactant poractant alfa is particularly suitable for being administered by a gastric tube. In particular its low viscosity allows administering the surfactant at a concentration of at least 40 mg/ml.

Advantageously, the dosage of the pulmonary surfactant to be administered is equal to or higher than 80 mg per kg body weight, preferably from 100 to 200 mg per kg body weight. The preferred dose is 100 mg per kg body weight.

The dosage of the surfactant to be administered varies with the size and maturity of the infant, as well as with the severity of the infant's condition. The skilled in the art will be readily able to determine these factors and to adjust the dosage administered via the thin tube.

After administration of the surfactant, the thin tube is removed.

However, the infant, depending on the severity of the individual condition and depending on the response of the infant to the first surfactant treatment, may receive a second dose of pulmonary surfactant. In particular, if the needed $FiO_2$ is higher than 40% the surfactant can be instilled by the thin tube, otherwise if the needed $FiO_2$ exceeds 60%, the surfactant can be instilled by endotracheal intubation under mechanical ventilation.

Said second dose may be equal to, higher or lesser than the first dose, depending on the needs and response of the infant.

The present invention is also directed to a kit comprising: comprising: a) a sterile pharmaceutical composition comprising a pulmonary surfactant having a viscosity lower than 20 centipoise suspended in a pharmaceutically acceptable aqueous medium at a concentration of at least 40 mg/ml; b) a thin tube having a diameter comprised between 5 and 12 Fr; c) a device for administering the surfactant at a controlled rate; and d) container means for containing the dosage form, the thin tube and the device.

Advantageously the sterile pharmaceutical composition is supplied as single-use glass vial.

Otherwise, in a particular embodiment, the sterile pharmaceutical composition can be supplied directly in the device used for administering the surfactant at a controlled rate.

The following examples illustrate the present invention.

EXAMPLES

Example 1

Viscosity Measurement of a Suspensions of Different Batches of Curosurf®

Rheological measurements were carried out at 25° C. with a rheometer SR 200 (Rheometric Scientific) and 40 parallel plate geometry using different batches of Curosurf®, i.e of poractant alfa suspended in physiological saline aqueous solution at a concentration of 80 mg/ml.

The instrument was calibrated to a gap of 0.7 mm.

The shear rate was varied between 0 and 500 $s^{-1}$.

For all batches Curosurf®, the viscosity ($\eta$) approaches a well-reproducible asymptotic value (max Shear Rate 500 $s^{-1}$) comprised between 6 and 10 mPas (1 mPas=1 centipoise).

Example 2

Administration of 100 mg/kg Dose Poractant alfa by Gastric Tube in Very-Low-Birth-Weight Infants Protocol of the Study In a preliminary observational study no difference between infants after surfactant application without intubation and infants with standard treatment was observed, despite the fact that infants treated with surfactant application without intubation were significantly smaller.

The primary objective of the following study is to demonstrate that the treatment of very-low-birth-weight (VLBW) infants with intratracheal instillation of a pulmonary surfactant is able to reduce the frequency of mechanical ventilation.

Secondary objectives of the study are to demonstrate that the proposed method:
is associated with a reduced duration and intensity of mechanical ventilation; and
is associated with a reduced incidence of bronchopulmonary dysplasia (BDP),
while being at least equivalent to standard treatment with regard to the secondary outcome measures death, intraventricular hemorrhage grade III and IV (IVH), and periventricular leukomalacia (PVL).

Design:
Prospective, randomized multi-center trial.
Study Population:
Inclusion Criteria:
gestational age 26±0–28=6 weeks,
birth weight below 1500 grams,
Age 0-12 hours,
Informed consent.
Exclusion Criteria:
Mechanical ventilation,
Participation in other studies.
Intervention:
Control-Group:
CPAP if $FiO_2$ exceeds 0.25,
all other therapies according to local standards.
Intervention Group:
CPAP if $FiO_2$ exceeds 0.25,
intratracheal surfactant via a gastric feeding tube if $FiO_2$ exceeds 0.3 (to keep oxygen saturation above 85%) and Silverman-score>4
all other therapies according to local standards.
Intervention:
Surfactant is given at a dose of 100 mg surfactant per kg body weight via a thin (gastric) tube into the trachea of the spontaneously breathing infant.
CPAP is applied continuously during the procedure (nasal IPPV may be applied).
Optional use of atropin (5 µg/kg body weight i.v.) prior to the procedure.
As many doctors will not use sedation for intubation in the delivery suite or in the first hours/minutes of life, sedation/analgesia is not mandatory and at the discretion of the individual neonatologist.
The gastric tube is placed with a Magill-forceps under direct visualization of the vocal cords by means of a laryngoscope.
After placement of the gastric tube, the laryngoscope is removed and surfactant (100 mg/kg body weight) is instilled into the trachea during 1-5 minutes.
Thereafter, the gastric tube is removed.
Close observation of the child during the procedure is mandatory.
Surfactant administration can be repeated if $FiO_2$ exceeds 0.4.
Intubation and intratracheal surfactant administration should be considered if $FiO_2$ exceeds 0.6 or the child suffers from severe respiratory distress.
All other treatments according to local standards.
Primary Outcome Measure:
Intubation and mechanical ventilation between the $25^{th}$ and $72^{th}$ hour of life or
$FiO_2$>0.6 (to keep oxygen saturation above 85%) between the $25^{th}$ and $72^{th}$ hour of life
$pCO_2$>65 mm Hg for more than two hours between the $25^{th}$ and $72^{th}$ hour of life.
Sample Size:
Based on current multi-center study data, we expect a frequency of the primary outcome measure in the control group of 60% vs. 40% in the intervention group. Since 50% of the infants are randomized to the control group, a total of 210 infants (105 in each group) will be necessary to test the primary hypothesis (p=0.05; beta-error 0.2; 2-sided). Since the participating centers are treating 250 patients/year who are eligible for the study and we calculated a 60% inclusion rate, a period of 30 months would be sufficient to test the primary hypothesis.

Secondary Outcomes:

Ventilation rate, IVH, PVL, BPD, death, operation due to retinopathy (ROP), patent ductus arteriosus (PDA), necrotizing enterocolitis (NEC), intestinal perforation, hydrocephalus and ventricular-peritoneal-shunt, number of surfactant doses, total surfactant (mg/kg bodyweight), days on assisted ventilation, days on supplemental oxygen, duration of hospitalization, weight gain per day, pneumothorax, other complications of prematurity (same definitions as for the genetic study).

Methods Against Bias:

Infants are randomized prior to intubation. To avoid the possible bias that infants in the intervention group are not intubated although they meet local intubation criteria, we defined a combined primary endpoint using a $FiO_2>0.6$ to gain a saturation>85% and/or $pCO_2>65$ mm Hg for more than two hours during the 25-72$^{th}$ hour of life as an indicator for treatment failure. $FiO_2$-levels and $pCO_2$ levels are observed and documented by nurses. Blinding and a sham procedure in the control group are not possible.

The invention claimed is:

1. A method for treating a respiratory distress syndrome in a spontaneously breathing pre-term infant in need of such treatment, said method comprising the steps of:
   a) applying nasal Continuous Positive Airway Pressure (nCPAP) with a nasal device to said infant at a pressure of from 1 to 12 cm water;
   b) introducing a tube selected from the group consisting of gastric tube, nasogastric tube, arterial or suction catheter and having an outer diameter of 5 Fr into the trachea of said infant;
   c) administering poractant alfa pulmonary surfactant suspended in a pharmaceutically acceptable aqueous medium through said tube and
   d) removing said tube
   wherein the surfactant suspension is applied at a concentration of from 40 mg/ml to 80 mg/ml and has a viscosity of between 5 and 15 mPas.

2. The method of claim 1 wherein the viscosity is comprised between 6 and 10 mPas.

3. The method of claim 1 wherein the surfactant is a modified natural surfactant or a reconstituted surfactant.

4. The method of claim 1 wherein nCPAP is applied with a nasal mask.

5. The method of claim 1 wherein the pressure is from 2 to 8 cm water.

6. The method of claim 1 wherein the surfactant is suspended in a buffered physiological saline aqueous solution.

7. The method of claim 6 wherein the surfactant is suspended in a volume of not more than 3 ml.

8. The method of claim 7 wherein the volume is not more than 2.5 ml.

9. The method of claim 1 wherein the respiratory distress syndrome is infant Respiratory Distress Syndrome (RDS).

10. The method of claim 1 wherein the respiratory distress syndrome is due to meconium aspiration or pulmonary infection.

11. A kit comprising: a) a sterile pharmaceutical composition having a viscosity of between 5 and 15 mPas comprising a poractant alfa pulmonary surfactant suspended in a pharmaceutically acceptable aqueous medium at a concentration of from 40 mg/ml to 80 mg/ml; b) a tube having an outer diameter of 5 Fr; c) a device for administering the surfactant at a controlled rate; d) container means for containing the pharmaceutical composition, the tube and the device.

12. The kit of claim 11 wherein the sterile pharmaceutical composition is supplied in a single-use glass vial.

13. The kit of claim 11 wherein the sterile pharmaceutical composition is supplied directly in the device used for administering the surfactant at a controlled rate.

* * * * *